US012653878B2

(12) United States Patent
Seele et al.

(10) Patent No.: US 12,653,878 B2
(45) Date of Patent: Jun. 16, 2026

(54) VACCINE COMPOSITION AGAINST STREPTOCOCCUS SUIS INFECTION

(71) Applicant: CEVA SANTE ANIMALE S.A., Libourne (FR)

(72) Inventors: Jana Seele, Hannover (DE); Christoph Baums, Leipzig (DE); Peter Valentin-Weigand, Iisede (DE)

(73) Assignee: CEVA SANTE ANIMALE S.A., Libourne (FR)

( * ) Notice: Subject to any disclaimer, the term of this patent is extended or adjusted under 35 U.S.C. 154(b) by 0 days.

(21) Appl. No.: 17/815,221

(22) Filed: Jul. 27, 2022

(65) Prior Publication Data

US 2022/0401543 A1 Dec. 22, 2022

Related U.S. Application Data

(60) Division of application No. 16/985,589, filed on Aug. 5, 2020, now Pat. No. 12,036,275, which is a continuation of application No. 15/314,597, filed as application No. PCT/EP2015/061961 on May 29, 2015, now abandoned.

(30) Foreign Application Priority Data

May 30, 2014 (EP) .................................... 14170637

(51) Int. Cl.
| | |
|---|---|
| *A61K 39/09* | (2006.01) |
| *A61K 39/00* | (2006.01) |
| *C07K 16/1275* | (2026.01) |

(52) U.S. Cl.
CPC ........ *A61K 39/092* (2013.01); *C07K 16/1275* (2013.01); *A61K 2039/53* (2013.01); *A61K 2039/54* (2013.01); *A61K 2039/543* (2013.01); *A61K 2039/545* (2013.01); *A61K 2039/552* (2013.01); *A61K 2039/575* (2013.01)

(58) Field of Classification Search
CPC .............. A61K 39/092; A61K 2039/53; A61K 2039/54; A61K 2039/543; A61K 2039/545; A61K 2039/552; A61K 2039/575; C07K 16/1275
See application file for complete search history.

(56) References Cited

U.S. PATENT DOCUMENTS

2017/0209561 A1 7/2017 Seele et al.

FOREIGN PATENT DOCUMENTS

WO WO 2004/020618 3/2004

OTHER PUBLICATIONS

Baums et al. (2009) Surface-associated and secreted factors of *Streptococcus suis* in epidemiology pathogenesis and vaccine development. Animal Health Research Reviews. 10(1):65-83.
Bork (Genome Research, 2000, 10:398-400) (Year: 2000).
Boslego et al (Vaccines and Immunotherapy, 1991, Chapter 17) (Year: 1991).
Bowie et al (Science, 1990, 257:1306-1310) (Year: 1990).
Burgess et al (J. of Cell Bio. 111:2129-2138, 1990) (Year: 1990).
Campbel, A. M. (Monoclonal Antibody Technology, Elsevier, NY. 1984; chapter 1, pp. 1-32) (Year: 1984).
Ellis (Vaccines, W.B. Saunders Company, Chapter 29, 1988, pp. 568-574) (Year: 1988).
Holden et al. (2009) Rapid evolution of virulence and drug resistance in the emerging zoonotic pathogen *Streptococcus suis*. PLOS One. 4(7)E6072:1-17.
Hulting et al. (2009) Two novel IgG endopeptidases of *Streptococcus equi*. FEMS Microbiology Letters. 298(1):44-50.
International Preliminary Report on Patentability corresponding to International Patent Application No. PCT/EP2015/061961 dated Dec. 6, 2016.
International Search Report corresponding to International Patent PCT/EP2015/061961 dated Jul. 27, 2015.
Lazar et al. (Molecular and Cellular Biology, 1988, 8:1247-1252) (Year: 1988).
Office Action corresponding to U.S. Appl. No. 15/314,597 dated Feb. 6, 2020.
Office Action corresponding to U.S. Appl. No. 15/314,597 dated May 2, 2019.
Office Action corresponding to U.S. Appl. No. 15/314,597 dated Nov. 24, 2017.
Office Action corresponding to U.S. Appl. No. 15/314,597 dated Sep. 13, 2018.
Seele et al. (2013a) Identification of a novel host-specific IgM protease in *Streptococcus suis*. Journal of Bacteriology. 195(5):930-940.
Seele et al. (2013b) Identification of a novel host-specific IgM protease in *Streptococcus suis*. Journal of Bacteriology. 195(5):930-940. Supplemental material.
Seele et al. (2015a) The immunoglobulin M-degrading enzyme of *Streptococcus suis*, IdeSsuis, is involved in complement evasion. Veterinary Research 46(1):45.
Seele et al. (2015b) The immunoglobulin M-degrading enzyme of *Streptococcus suis*, IdeSsuis, is a highly protective antigen against serotype 2. Vaccine. 33(19):2207-2212.

(Continued)

*Primary Examiner* — Robert A Zeman
(74) *Attorney, Agent, or Firm* — Oblon, McClelland, Maier & Neustadt, L.L.P.

(57) ABSTRACT

Described is a vaccine composition comprising an effective amount of at least one polypeptide selected from the group of IdeSsuis, rIdeSsuis, an analogue or a fragment thereof, or a polynucleotide encoding the same. This vaccine composition is used in the prophylactic, metaphylactic or therapeutic treatment of a *Streptococcus suis* infections in pigs or humans.

3 Claims, 5 Drawing Sheets

Specification includes a Sequence Listing.

(56)                    References Cited

OTHER PUBLICATIONS

Skolnick et al. (Trends in Biotechnology 18: 34-39, 2000) (Year: 2000).

UniProt Accession No. B9WTH0; [Online] (Apr. 14, 2009) SubName: Full=Mac 1 domain protein {EC0:0000313:EMBL:EEF65121.1} Flags:Precursor.

UniProt Accession No. C5W022 [Online] (Sep. 2009) RecName: Full=IgM protease; EC=3.4.22.-; AltName: Full=Immunoglobulin M-degrading enzyme of S. suis; Short=IdeSsuis; Flags:Precursor; retrieved from EBI accession No. UNIPROT:C5W022. Database accession No. C5W022 sequence.

Wisselink et al. (2001) Protection of Pigs Against Challenge with Virulent Streptococcus suis Serotype 2 Strains by a Muramidase-Released Protein and Extracellular Factor Vaccine. Veterinary Record. British Veterinary Association. 148(15):473-477.

Written Opinion of the International Searching Authority corresponding to International Patent Application No. PCT/EP2015/061961 dated Dec. 3, 2015.

Zhang et al. (2011) Comparative genomic analysis of Streptococcus suis reveals significant genomic diversity among different serotypes. BMC Genomics. Biomed Central Ltd. 12(1):523.

Search Report issued May 31, 2022, in corresponding Maylaysian Patent Application No. PI2020000533.

Christoph Georg Baums et al, "Surface-Associated and Secreted Factors of Streptococcus suis in Epidemiology, Pathogenesis and Vaccine Development", Animal Health Research Reviews, vol. 10, No. 1, Jun. 1, 2009, pp. 65-83.

Greta Hulting et al, "Two Novel IgG Endopeptidases of Streptococcus equi", FEMS Microbiology Letters, Vo. 298, No. 1, Sep. 1, 2009, pp. 44-50.

Anding Zhang, et al, "Comparative Genomic Analysis of Streptococcus suis Reveals Significant Genomic Diversity Among Different Serotypes", BMC Genomics Biomed Central Ltd. London, UK, vol. 12, No. 1., Oct. 25, 2011 pp. 523.

Matthew T.G. Holden, et al., "Rapid Evolution of Virulence and Drug Resistance in the Emerging Zoonotic Pathogen Streptococcus suis", PLOS ONE, vol. 4, No. 7, Jul. 2009, pp. 1-17.

Canadian Office Action issued on Mar. 18, 2022 in Patent Application No. 2,947,798, 4 pages.

| number of pigs | 1. immunization | 2. immunization | challenge |
|---|---|---|---|
| 9 | rideSsuis (0.4mg/piglet) | rideSsuis (0.25mg/piglet) + bacterin (S. suis serotype 2 strain [9841) | S. suis serotype 2 strain 10 |
| 9 | rideSsuis (0.4mg/piglet) | rideSsuis (0.25mg/piglet) | S. suis serotype 2 strain 10 |
| 8 | placebo | bacterin (S. suis serotype 2 strain [9841) | S. suis serotype 2 strain 10 |
| 9 | placebo | placebo | S. suis serotype 2 strain 10 |

- vs. prime bacterin : *p*=0.8237
- vs. prime and booster rideSsuis: *p*=0.0031
- vs. prime and booster rideSsuis + prime bacterin: *p*=0.0013 prime bacterin vs. prime and booster rideSsuis: *p*=0.0031 prime bacterin vs. prime and booster rideSsuis + prime bacterin: *p*=0.0013

| group | number of pigs | 1. immunization | 2. immunization | bactericidal assay | |
|---|---|---|---|---|---|
| 1 | 9 | Placebo (PBS plus adjuvant) | Placebo (PBS plus adjuvant) | Serotype 2 (St. 10) | Serotype 9 (A3286/94) |
| 2 | 9 | rideSsuis (0.25mg/piglet) | rideSsuis (0.25mg/piglet) | Serotype 2 (St. 10) | Serotype 9 (A3286/94) |

| group | number of pigs | 1. immunization | 2. immunization | bactericidal assay |
|---|---|---|---|---|
| 1 | 6 | no immunization | no immunization | S. *suis* serotype 9 strain A3286/94 |
| 2 | 6 | rIdeSsuis_homologue (0.5mg/piglet) | rIdeSsuis_homologue (0.5mg/piglet) | S. *suis* serotype 9 strain A3286/94 |
| 3 | 6 | rIdeSsuisB2 (0.25mg/piglet) | rIdeSsuisB2 (0.25mg/piglet) | S. *suis* serotype 9 strain A3286/94 |
| 4 | 5 | rIdeSsuis (0.25mg/piglet) | rIdeSsuis (0.25mg/piglet) | S. *suis* serotype 9 strain A3286/94 |

VACCINE COMPOSITION AGAINST *STREPTOCOCCUS SUIS* INFECTION

CROSS-REFERENCE TO RELATED APPLICATIONS

This application is a divisional of U.S. patent application Ser. No. 16/985,589 filed on Aug. 5, 2020, pending, which is a continuation of U.S. patent application Ser. No. 15/314, 597, filed Nov. 29, 2016, abandoned, which is a U.S. National Stage application of PCT International Patent Application Serial No. PCT/EP2015/061961, filed May 29, 2015, which itself claims benefit of European Patent Application Serial No. 14170637.4, filed May 30, 2014, each of which is incorporated herein by reference in its entirety.

The .xml file of the sequence listing designated "541470US.xml, was generated on Jul. 20, 2022, and is 36,864 bytes in size. It is hereby incorporated by reference for all purposes.

FIELD OF THE INVENTION

The present invention relates to a vaccine composition and the use thereof for immunization and protection of mammals, in particular pigs and humans, against *Streptococcus suis*.

BACKGROUND OF THE INVENTION

*Streptococcus suis* (*S. suis*) colonizes the respiratory, alimentary and genital tract of pigs. *S. suis* is also one of the most important porcine pathogens, causing different pathologies such as meningitis, septicaemia, arthritis and endocarditis.

*S. suis* infections account for high production losses in the swine industry worldwide. Antibiotics are commonly used to treat *S. suis* infections. But recurrent infections frequently occur as well as the ongoing discussions concerning the reduction of antibiotic usage underline the need for alternative control measures. In Europe, no licensed vaccine is available but autologous bacterins are commonly used. A major drawback is the fact that these vaccines protect only against the homologous serotype. But *S. suis* is a very diverse organism and different serotypes are responsible for morbidity in piglets. Especially serotype 2 strains play an important role for diseases in piglets worldwide.

*S. suis* serotype 2 has been identified to cause meningitis in adults in Asia, but to date no transmission of *S. suis* between humans has been detected.

In general infections elicit an early antigen-specific Immunoglobulin M (IgM) response leading to affinity maturation and isotope switching. Further, IgM antibodies present prior to infection, which are naturally occurring, are important in linking innate to adaptive immunity.

In pigs, IgM is especially important as monomeric membrane IgM (mIgM) as it is the only B-cell receptor occurring since IgD is missing in pigs. Further, IgM synthesis in newborn piglets starts much earlier than IgG and IgA synthesis. IgM in colostrum is crucial for the protection against pathogens which is carried out by complement-mediated killing. Therefore IgM antibodies are important in the protection against different pathogens.

Various virulence or virulence-associated factors of *S. suis* serotype 2 have been identified, among the capsule which is so far the only known essential virulence factor protecting the pathogen against phagocytosis. A number of surface-associated and secreted proteins of *S. suis* serotype 2 exhibit the same or very similar functions as homologous factors of other pathogenic streptococci. A variety of human or animal pathogens such as *Streptococcus pyogenes, Streptococcus equi* subspecies *equi* and *Streptococcus equi* subspecies *zooepidemicus* express specific IgG endopeptidases which are homologue to each other.

A surface-associated or secreted factor with a function unique for *S. suis* has been firstly described by Seele et al. ("Identification of a Novel Host-specific IgM Protease in *Streptococcus suis.*" 2013; Journal of Bacteriology, 195: 930-940). Seele et al. showed that this IgM protease, designated IdeSsuis, does not function as an IgG endopeptidase. The IgM protease degrades opsonising IgM on the bacterial surface and therefore promotes the survival of *S. suis* in blood of bacterin-primed piglets. IdeSsuis is highly specific for IgM and does not cleave IgG or IgA. Seele et al., however, are silent on the function of IdeSsuis, rIdeSsuis and analogues and fragments thereof as effective vaccine against *S. suis* infections. It is merely hypothesized that neutralization of the IdeSsuis IgM protease activity might substantially improve the protective efficacy of bacterins or other future vaccines inducing opsonizing antibodies. However, it is not disclosed that IdeSsuis and related proteins may be used as the exclusive immunizing agent in a vaccine against *S. suis* infections.

Baums et al. disclose in *Surface-associated and secreted factors of Streptococcus suis in epidemiology, pathogenesis and vaccine development, Animal Health Research Reviews*, Volume 10, Issue 01, June 2009, pp 65-83 bacterial factors, both surface-associated and secreted ones, which are considered to contribute to *S. suis* interaction(s) with host factors and cells. Factors are presented with respect to (i) their identification and features, (ii) their distribution among *S. suis* and (iii) their significance for virulence, immune response and vaccination. This review emphasizes the numerous challenging questions remaining to be answered in the future.

The problem to be solved according to the invention is to overcome the problems described in the art and to provide a new vaccine composition to immunize and protect mammals, in particular pigs and humans, against *S. suis* infections.

SUMMARY OF THE INVENTION

This problem is solved, according to the present invention, by providing a vaccine composition which comprises an effective amount of at least one polypeptide or at least one vector selected from the group of (a) a protein designated IdeSsuis, an analogue or a fragment thereof, (b) a protein designated rIdeSsuis, an analogue or a fragment thereof, (c) a vector with a polynucleotide inserted therein encoding the protein IdeSsuis, an analogue or a fragment thereof, (d) a vector with a polynucleotide inserted therein encoding the protein rIdeSsuis, an analogue or a fragment thereof and at least a pharmaceutical carrier, a diluent or an adjuvant.

DETAILED DESCRIPTION OF THE INVENTION

The vaccine composition used in the present invention contains at least one sole polypeptide defined by (a) or (b) together with a pharmaceutical carrier or a diluent or an adjuvant or a mixture thereof. Further the vaccine may also comprise at least one sole vector defined by (c) or (d) with a pharmaceutical carrier, a diluent or an adjuvant or a mixture thereof.

Preferred is a vaccine composition, according to the present invention, wherein IdeSsuis of (a) comprises (a.a) the amino acid sequence of SEQ ID NO: 1;

(a.b) a fragment or an analogue of the amino acid sequence of SEQ ID NO: 1; or (a.c) a fragment of either (a.a) or (a.b) having an IgM protease activity.

Further preferred is a vaccine composition, according to the present invention, wherein rIdeSsuis of (b) comprises or consists of (b.a) the amino acid sequence of SEQ ID NO: 2, 6 or 7;

(b.b) a fragment or an analogue of the amino acid sequence SEQ ID NO: 2, 6 or 7;

(b.c) an amino acid sequence lacking the amino acids from position 1 to 34 of the amino acid sequence SEQ ID NO: 1;

(b.d) an amino acid sequence which is at least 60% homologue, preferably 70% homologue and most preferably 85% homologue to the amino acid sequence of the protein IdeSsuis of SEQ ID NO: 1;

(b.e) a fragment of either (b.a) or (b.b) or (b.c) or (b.d) having an IgM protease activity; or (b.f) a fragment of either (b.a) or (b.b) or (b.c) or (b.d) comprising or consisting of the amino acid sequence of SEQ ID NO: 5 or an amino acid sequence which is at least 95% homologous thereto.

The amino acid sequence of SEQ ID NO: 2 represents the sequence of SEQ ID NO: 1, however lacking amino acids 1-34 (signal peptide) but adding a HIS tag. It is noted that SEQ ID NO: 1 was derived from the serotype 2 strain of *S. suis*.

The amino acid sequence of SEQ ID NO: 6 represents the N terminal sequence of SEQ ID NO: 2.

SEQ ID NO: 7 (also called antigen rIdeSsuisB2) contains the complete amino acid sequence of the mature IdeSsuis protein of a *S. suis* serotype7 strain but adding a N terminal HIS tag. IdeSsuis protein of a *S. suis* serotype7 strain differs in the C terminal half of the protein since it lacks a sequence of 114 amino acids compared to SEQ ID NO: 1. Amino acids 80 to 414 of SEQ ID NO: 7 (highly conserved part of the so-called Mac-1 domain) correspond in 97.9% to the sequence of SEQ ID NO: 5. The overall identity between SEQ ID NO: 7 and 1 is 96.4% (not considering the N terminal HIS tag and the gap of 114 amino acids).

The term "fragment or analogue" as used herein is defined as follows:

An "analogue" can be regarded as an amino acid sequence similar to the ones disclosed above and showing a level of homology of at least 60%, preferably 70% and most preferably 85% to the original amino acid sequence (e.g. SEQ ID NO: 1, 2, 6 or 7). Also higher degrees of homology, such as 95%, are contemplated herein. Homology, as used herein, means identity. As such, the sequences might differ from each other based on substitution, deletion or insertion.

The degree of identity can be determined with the protein blast program using the blastp algorithm with default parameters which are, for example, Expect threshold: 10, Word size: 3, Matrix: BLOMSUM62, Gap Costs: Existence: 11 Extension: 1 and Compositional adjustments: Conditional compositional score matrix adjustment (BLAST is a registered trademark of the National Library of Medicine). The program can be used to search a protein database using a protein query. Identity reports the exact matches between aligned query and database sequences.

Preferably, amino acid "substitutions" are the result of replacing one amino acid with another amino acid having similar structural and/or chemical properties, i.e., conservative amino acid replacements.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, praline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1, 2 or 3 amino acids. The variation allowed may be experimentally determined by systematically making insertions or deletions of amino acids in a protein using recombinant DNA techniques and assaying the resulting recombinant variants for activity. This does not require more than routine experiments for a skilled person.

An "analogue" may alternatively or in addition be defined as an amino acid sequence similar to the ones disclosed above and comprising the highly conserved part of the Mac-1 domain (SEQ ID NO: 5) or an amino acid sequence which is at least 95% homologous thereto. The inventors surprisingly found that this domain is mainly responsible for the unexpected immunogenic activity of IdeSsuis proteins and, for itself, is sufficient to provide immune protection to the vaccinated animal. Different serotypes of *S. suis* are existing which partially show large variations in their amino acid sequence thus leading to a level of homology down to about 60%. However, the highly conserved Mac-1 domain shows only small variations between the different serotypes, for example 97.9% between serotype strains 2 and 7.

Therefore, it is acceptable that the amino acids of the present invention (and the nucleic acids encoding the same) show a higher level of variation outside the Mac-1 domain than inside.

The term "fragment" can be defined in a similar way (see above). It describes a shorter amino acid sequence than an analogue (less than about 400 amino acids). It contains or consists of the highly conserved part of the Mac-1 domain (SEQ ID NO: 5) or an amino acid sequence which is at least 95% homologous thereto. Optionally, a fragment can be defined as having an IgM protease activity, although this is not an essential requirement.

These fragments may be used as the exclusive active ingredient in a vaccine according to the present invention.

Thus, the vaccine composition of the present invention in a preferred embodiment comprises, essentially consists of or consists of a protein comprising or consisting of the amino acid sequence of SEQ ID NO: 5 or an amino acid sequence which is at least 95% homologous thereto. In an even more preferred embodiment, the protein (or vector encoding the same) is the only active or immunogenic ingredient.

The term "comprising" as used herein in the context of the vaccine composition means that further active or immunogenic components can be present. "Consisting of" means that no further components are present and "essentially consisting of" means that specific further components can be present, namely those not materially affecting the essential characteristics of the vaccine (i.e. inactive or not immunogenic ingredients).

In a preferred embodiment, the present invention provides a vaccine composition essentially consisting of an rIdeSsuis protein which is at least 60%, 70%, 85% or 95% homologous to the amino acid sequence of the protein IdeSsuis of SEQ ID NO: 1 and/or comprises or consists of the amino acid sequence of SEQ ID NO: 5 or an amino acid sequence which is at least 95% homologous thereto.

The above definitions are mutatis mutandis also applicable to the nucleic acid sequences of the present invention encoding these proteins. The homology definitions are the same, the fragment length would be less than about 1,200 nucleic acids.

Further preferred is a vaccine composition, according to the present invention wherein a fragment of the effective amount of said polypeptide of (a) or (b) is part of a fusion protein with at least one other protein.

Preferred is a vaccine composition, according to the present invention, wherein the polynucleotide of (c) comprises a sequence encoding a protein defined as IdeSsuis, namely (a.a) the amino acid sequence of SEQ ID NO: 1;

(a.b) a fragment or an analogue of the amino acid sequence of SEQ ID NO: 1: or (a.c) a fragment of either (a.a) or (a.b) having an IgM protease activity.

Especially preferred is a vaccine composition, according to the present invention, which is characterized in that the polynucleotide comprises (c.a) a sequence of SEQ ID NO: 3 or a complementary sequence thereto; (c.b) a fragment of the sequence of (c.a) or (c.c) a fragment of the sequence of (c.a) which encodes a protein having IgM protease activity.

Further preferred is a vaccine composition, according to the present invention, wherein the polynucleotide of (d) comprises a sequence encoding a protein defined as rIdeSsuis, namely (b.a) the amino acid sequence of SEQ ID NO: 2;

(b.b) a fragment or an analogue of the amino acid sequence SEQ ID NO: 2;

(b.c) an amino acid sequence lacking the amino acids from position 1 to 34 of the amino acid sequence SEQ ID NO: 1;

(b.d) an amino acid sequence which is at least 60% homologue, preferably 70% homologue and most preferably 85% homologue to the amino acid sequence of the protein IdeSsuis of SEQ ID NO: 1; or (b.e) a fragment of either (b.a) or (b.b) or (b.c) or (b.d) having a IgM protease activity, and/or (b.f) a fragment of either (b.a) or (b.b) or (b.c) or (b.d) comprising or consisting of the amino acid sequence of SEQ ID NO: 5 or an amino acid sequence which is at least 95% homologous thereto.

Especially preferred is a vaccine composition, according to the present invention, which is characterized in that the polynucleotide comprises (d.a) a sequence of SEQ ID NO: 4, 8 or 9 or a complementary sequence thereto;

(d.b) a fragment of the sequence of (d.a) or (d.c) a fragment of the sequence of (d.a) which encodes a protein having IgM protease activity Preferred is a vaccine composition, according to the present invention, wherein the polynucleotide is cDNA, DNA or cRNA, RNA. The term "nucleic acid sequence"

refers to a heteropolymer of nucleotides or the sequence of these nucleotides. The terms "nucleic acid" and "polynucleotide" are used interchangeably herein to refer to a heteropolymer of nucleotides.

Further it is preferred that a vaccine composition, according to the present invention, is further characterized by the polynucleotide integrated into a vector, wherein the polynucleotide is operably linked to an expression control region of the vector.

This expression vector preferably comprises one or more regulatory sequences. The term "expression vector" generally refers to a plasmid or phage or virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

It is also preferred that a vaccine composition, according to the present invention, is provided in a physiologically administrable form and is suitable for intramuscular, intravenous, subcutaneous or dermal injection or mucosal application. It is noted that an intravenous administration is less preferred.

In a further aspect, the present invention is directed to a fragment of IdeSsuis having the amino acid sequence of SEQ ID NO: 5, or an amino acid sequence which is at least 95% homologous thereto. SEQ ID NO: 5 corresponds to the highly conserved part of the Mac-1 domain. Although this domain shows an IgM protease activity, the immunogenic effect is not necessarily linked to this activity. For example, within the scope of the present invention are analogues of SEQ ID NO: 5 where the active center of the protease has been inactivated by mutagenesis of the Cys-residue. Also in this case, the analogue will be effective as a vaccine for eliciting an immune response.

Furthermore, it turned out that amino acid sequences may be effective as a vaccine against *S. suis* infections if they maintain a homology of at least 95% to SEQ ID NO: 5. This includes substitution, insertion or deletion of single amino acids. It turned out that natural occurring Mac-1 domains, although showing some variations, do not differ by more than 5%, or in other words, share an identity of 95% or more in this domain. Exemplary *Streptococcus suis* sequences were obtained from strains isolated in different geographic regions (America, Asia, Europe) and were derived from different host organisms (humans, pigs). These strains belong to different serotypes (1 to 4, 7 to 9, 14 and 16 or which were non-typeable). This is summarized in the enclosed table 1:

| Protein ID | Identity SEQ ID NO: 5 | Strain(s) | Isolated from species | Geographic origin | Serotype |
|---|---|---|---|---|---|
| WP_011922092 | 100% | 05ZYH33 | Human | China | 2 |
| | | P 1/7 | Pig | Europe | 2 |
| | | S15W | Pig | United Kingdom | 9 |
| | | S12W | Pig | United Kingdom | 14 |
| WP_044670034 | 100% | E10N | Pig | Vietnam | 2 |
| | | E30Y | Human | Vietnam | 2 |
| WP_012775646 | 100% | JS14 | Pig | China | 14 |
| WP_044671938 | 99% | LSOC | Pig | United Kingdom | 1 |
| WP_002935529 | 98% | 89-1591 | Pig | Canada | 2 |
| | | D9 | Pig | China | 7 |
| | | LL-S | Pig | United Kingdom | 3 |
| WP_015647040 | 98% | TL13 | Pig | China | 16 |
| WP_023370787 | 97% | T15 | Pig | Netherlands | 2 |
| | | S97A | Pig | United Kingdom | 4 |
| | | S16Z | Pig | United Kingdom | 8 |
| WP_044678723 | 96% | LS1B | Pig | United Kingdom | Non-typeable |

The sequence information on the Mac-1 domain of proteins WP_044671938, WP_002935529, WP_015647040, WP_023370787 and WP_044678723 is disclosed in SEQ ID NO: 10 to SEQ ID NO: 14.

Since their homology to SEQ ID NO: 5 is higher than 95% they are falling within the definition of a fragment or homologue of the present invention.

A still further aspect is an rIdeSsuis protein comprising the amino acid sequence of SEQ ID NO: 6 or 7, or an amino acid sequence which is at least 60%, preferably 70%, 85% or 95% homologous to the amino acid sequence of the protein IdeSsuis of SEQ ID NO: 6 or 7.

Another object of the present invention is a host cell which is transfected with the vector.

A further object of the present invention is a method for producing a protein defined as rIdeSsuis as a guest antigen in a vector or a different organism, respectively a host cell transfected under condition suitable for expression of said recombinant protein.

A further aspect of the present invention is an antibody which recognizes an IdeSsuis or rIdeSsuis protein, analogue or fragment has defined above.

The antibody is preferably selected from a group, which consists of polyclonal antibodies, monoclonal antibodies, humanized antibodies, chimeric antibodies and synthetic antibodies.

The term "antibody", is used herein for intact antibodies as well as antibody fragments, which have a certain ability to selectively bind to an epitope. Such fragments include, without limitations, Fab, F(ab') 2 and Fv antibody fragments. The term "epitope" means any antigen determinant of an antigen, to which the paratope of an antibody can bind. Epitope determinants usually consist of chemically active surface groups of molecules (e.g. amino acid or sugar residues) and usually display a three-dimensional structure as well as specific physical properties.

The antibodies according to the invention can be produced according to any known procedure. For example the pure complete IdeSsuis or rIdeSsuis protein according to the invention or a fragment/analogue of it can be produced and used as immunogen, to immunize an animal and to produce specific antibodies.

The production of polyclonal antibodies is commonly known. Detailed protocols can be found for example in Green et al, Production of Polyclonal Antisera, in *Immunochemical Protocols* (Manson, editor), pages 1-5 (Humana Press 1992) and Coligan et al, Production of Polyclonal Antisera in Rabbits, Rats, Mice and Hamsters, in *Current Protocols In Immunology*, section 2.4.1 (1992). In addition, the expert is familiar with several techniques regarding the purification and concentration of polyclonal antibodies, as well as of monoclonal antibodies (Coligan et al, Unit 9, *Current Protocols in Immunology*, Wiley Interscience, 1994).

The production of monoclonal antibodies is as well commonly known. Examples include the hybridoma method (Kohler and Milstein, 1975, Nature, 256:495-497, Coligan et al., section 2.5.1-2.6.7; and Harlow et al., *Antibodies: A Laboratory Manual*, page 726 (Cold Spring Harbor Pub. 1988).), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

In brief, monoclonal antibodies can be attained by injecting a mixture which contains the protein according to the invention into mice. The antibody production in the mice is checked via a serum probe. In the case of a sufficient antibody titer, the mouse is sacrificed and the spleen is removed to isolate B-cells. The B cells are fused with myeloma cells resulting in hybridomas. The hybridomas are cloned and the clones are analyzed. Positive clones which contain a monoclonal antibody against the protein are selected and the antibodies are isolated from the hybridoma cultures. There are many well established techniques to isolate and purify monoclonal antibodies. Such techniques include affinity chromatography with protein A sepharose, size-exclusion chromatography and ion exchange chromatography. Also see for example, Coligan et al., section 2.7.1-2.7.12 and section "Immunoglobulin G (IgG)", in *Methods In Molecular Biology*, volume 10, pages 79-104 (Humana Press 1992).

Preferably, the present invention provides humanized IdeSsuis or rIdeSsuis specific mouse antibodies.

The above antibodies may form part of a parenteral composition for therapeutic treatment of a human or animal (pig) patient suffering from a *S. suis* infection. However, it might be used for prophylactic purposes as well.

In a still further aspect, the present invention is directed to the use of the proteins as disclosed hereinabove for producing the above described antibodies.

Another object of the present invention is the use of the vaccine or parenteral composition, according to the present invention, to perform a prophylactic or metaphylactic or therapeutic treatment of a *Streptococcus suis* infection in pigs. It is further contemplated herein to use the vaccine or the parenteral composition of the present invention for prophylactic or metaphylactic or therapeutic treating an *S. suis* infection in a human patient.

Especially preferred is the use of the vaccine composition, according to the present invention, wherein the treatment causes an immunological response in pigs whereas the immunological response is the activation of a humoral and cellular response against the protein IdeSsuis produced by *Streptococcus suis*.

The treatment (vaccination) involves at least one or two immunizations. The overall dosage administered per pig/human is about 0.05-2.0 mg of protein.

The preparation of the vaccine composition according to the invention is known in the art, and is described in handbooks known to the person skilled in the art. For the production of the vaccine composition according to the present invention pharmaceutically acceptable carriers, diluents or adjuvants which can be used which comprise but are not limited to the following: mineral salt adjuvants (e.g., alum-, calcium-, iron-, zirconium-based), tensoactive adjuvants (e.g., Quil A, QS-21, other saponins), bacteria-derived adjuvants (e.g., N-acetyl muramyl-L-alanyl-D-isoglutamine (MOP), lipopolysaccharides (LPS), monophosphoryl lipid A, trehalose dimycolate (TDM), DNA, CpGs, bacterial toxins), adjuvant emulsions (e.g., FIA, Montanide, Adjuvant 65, Lipovant), liposome adjuvants, polymeric adjuvants and carriers, cytokines (e.g., Granulocyte-macrophage colony stimulating factor), carbohydrate adjuvants, living antigen delivery systems (e.g., bacteria, viruses). Furthermore carriers can also comprise dry formulations such as coated patches made from titan or polymer.

Techniques for formulation and administration of the vaccines of the present application may also be found in "Remington, The Science and Practice of Pharmacy", 22nd edition.

Thus, the present invention is directed to a vaccine composition comprising a protein designated as IdeSsuis or rIdeSsuis or a fragment of either thereof; or a polynucleotide either expressing the protein IdeSsuis or rIdeSsuis or a fragment either thereof which is integrated into an expression vector, whereas the recombinant protein is preferred.

The inventors detected the following:

(a) the induction of opsonising antibodies is crucial for the protective efficacy of a *S. suis* bacterin.

(b) IdeSsuis promotes survival of *S. suis* in blood of vaccinated piglets.

Further the inventors showed, that the vaccination of pigs using the protein rIdeSsuis alone as the sole antigen provides a protection for pigs infected by *S. suis*. According to the invention vaccination with rIdeSsuis prevents the cleavage of IgMs by the IdeSsuis IgM protease of *S. suis* by inducing neutralizing antibodies.

According to the invention, the vaccination of pigs with the recombinant protein rIdeSsuis or a fragment thereof led to high titers of IdeSsuis-specific IgG antibodies with neutralizing activity in contrast to reconvalescent or *S. suis* bacterin immunized piglets. Further, according to Example 1, it has been shown that rIdeSsuis provides a higher immunity against *S. suis* infections than prior art bacterin vaccines.

Further the inventors showed, that the vaccination of pigs with the recombinant protein rIdeSsuis or an analogue or fragment thereof reduces the survival of *S. suis* in the blood.

One important aspect of the present invention—as noted above—resides in the surprising insight that the proteins, nucleic acids and their analogues and fragments as defined hereinabove may be used as the only immunogenic agent for providing protection against *S. suis* infections. No other active ingredients are required, such as bacterins etc. used in the prior art. This is supported by the experimental evidence provided in Example 2. It was shown that the vaccines according to the present invention have a dramatically enhanced efficacy versus placebo/control vaccines, see the Bactericidal Assay data of trials 1 and 2 of Example 2 (FIGS. 3 and 4). The conclusions which can be drawn from the experimental results are as follows:

rIdeSsuis (SEQ ID NO: 2) provides immune protection across different serotypes of *S. suis.*

A protein at least containing the highly conserved Mac-1 domain (SEQ ID NO: 5) is sufficient to provide immune protection, Also IdeSsuis proteins of other serotypes, at least containing the highly conserved Mac-1 domain (SEQ ID NO: 5) induce protection, even if their overall sequence outside this domain differs from that of the serotype 2 strains (even if certain sequence segments are entirely absent).

According to the present invention, the proteins IdeSsuis or rIdeSsuis or analogues/fragments thereof can also be used in fusion proteins. Fusion proteins are created by joining two or more genes which are originally coded for separate proteins. The translation of this fusion gene results in a single or multiple polypeptide with functions derived each from the originally proteins. In the state of the art, fusion proteins are often used to simplify specific applications, such as detection, integration or transport of the protein of interest. A prominent member for detection by fluorescent microscopy is the green fluorescent protein (GFP) fused to the protein of interest.

Other proteins which could be fused to IdeSsuis to improve the delivery and immunogenicity of the antigen are immunoglobulin FC-fragment, non-toxic cholera toxin CTA subunit, mutated heat-labile toxins, *Bacillus subtilis* spore coat protein or bacterial flagellins. Furthermore fusion proteins with proteins of viruses or phages (e.g. modified vaccinia virus Ankara (MVA), Hepatitis B virus, Lambda phage or filamentous bacteriophages like fd, M13 or fl) can be used for the expression of IdeSsuis on the surface of a virus particle or a virus-like particle.

Another possibility to detect fusion proteins is the usage of so called protein tags which are often used during the production of fusion proteins respectively their purification and detection by performing affinity chromatography, western blotting, immunohistochemistry or fluorescent microscopy. Protein tags are commonly short amino acid sequences for example HIS-Tag, myc-Tag, HA-Tag, Step-Tag, GST-Tag, maltose binding protein-Tag or Thioredoxin-Tag.

The method for producing recombinant proteins such as rIdeSsuis, fragments or analogues thereof, according to the present invention is known by the person skilled in the art and also described by handbooks known by the person skilled in the art. In general host cells are used for being transfected with a vector encoding the protein of interest for production of a recombinant protein. In general those host cells may be bacteria (e.g *E. coli, Bacillus* or *Lactococcus* strains), human (e.g. 293-T, HEK-293), mouse cell lines, insect cell lines, yeast cells or plant based systems.

For the transfection of host cells expression vectors such as plasm ids (e.g pET, pQE), viruses and phages (e.g. baculovirus. Lambda phage or filamentous bacteriophages) can be used.

Typically vaccine or parenteral compositions are prepared as injectables, either as liquid solutions or suspensions.

The subject of the present invention is also a vaccine or parenteral composition for subcutaneous, intravenous, intramuscular, dermal or mucosal application.

The present vaccines are used to perform a prophylactic or metaphylactic or therapeutic treatment of a *Streptococcus suis* infection in pigs or humans. The treatment involves at least one, preferably two immunizations. Although one single immunization is preferred in practice, a standard immunization usually comprises a prime-boost regimen, i.e. 2 distinct vaccinations. The boost vaccination usually is given in a time frame of 1-3, preferably about 2 weeks after the prime vaccination. The dosage of the individual vaccinations might be the same or different, although it is preferred that the vaccine dosage of both is identical.

The overall dosage which has to be administered to the animal or human patient is about 0.05-2.0 mg of IdeSsuis or rIdeSsuis protein, analogues or fragments as defined here-inabove. Preferred dosages include 0.1-1.0, more preferably about 0.5 mg. This dosage is administered in one dosage should one single vaccination be sufficient. If more than one vaccination is applied, the overall dosage is split in several equal sub-dosages, for example, if two vaccinations are used, the individual dosage of the vaccination is about 0.025-1.0 mg of protein.

The present invention is further described with reference to the following figures, where FIG. 1 shows a time table representing the vaccination challenge experiments with *S. suis* in pigs, FIG. 2 shows a graph representing the results gained with the vaccination challenge experiments of FIG. 1, FIG. 3 shows a diagram of a bactericidal assay involving vaccination with placebo vs. rIdeSsuis, and FIG. 4 depicts a diagram of a bactericidal assay involving vaccination with rIdeSsuis or rIdeSsuis analogues vs. a control group.

Further, a Sequence Listing is attached to this description.

SEQ ID NO: 1 shows the amino acid sequence of the protein IdeSsuis;

SEQ ID NO: 2 shows the amino acid sequence of the recombinant protein rIdeSsuis without the signal peptide;

SEQ ID NO: 3 shows the nucleotide sequence coding for IdeSsuis and SEQ ID NO: 4 shows the nucleotide sequence coding for rIdeSsuis.

SEQ ID NO: 5 shows the amino acid sequence of the highly conserved part of the Mac-1 domain of IdeSsuis.

SEQ ID NO: 6 shows the amino acid sequence of the rIdeSsuis analogue rIdeSsuis_homologue. SEQ ID NO: 7 shows the amino acid sequence of the rIdeSsuis analogue rIdeSsuisB2.

SEQ ID NO: 8 shows the nucleotide sequence coding for rIdeSsuis analogue rIdeSsuis_homologue.

SEQ ID NO: 9 shows the nucleotide sequence coding for rIdeSsuis analogue rIdeSsuisB2.

SEQ ID NO: 10 shows amino acid sequence of amino acids 91 to 425 of WP 044671938.

SEQ ID NO: 11 shows amino acid sequence of amino acids 91 to 425 of WP_002935529.

SEQ ID NO: 12 shows amino acid sequence of amino acids 92 to 426 of WP_015647040.

SEQ ID NO: 13 shows amino acid sequence of amino acids 92 to 426 of WP_023370787.

SEQ ID NO: 14 shows amino acid sequence of amino acids 92 to 426 of WP_044678723.

The following examples shall explain the present invention. The examples shall be understood only as one preferred embodiment of the invention. It is not intended to limit the present invention to the scope of the given examples.

Example 1

The following example provides experimental data after performing vaccination challenge experiments in piglets infected by *S. suis*.

Establishment of vaccination challenge experiments in piglets for different *S. suis* serotypes (serotype 2 and 9) and infection routes (intravenous and intranasal).

Figure 1:
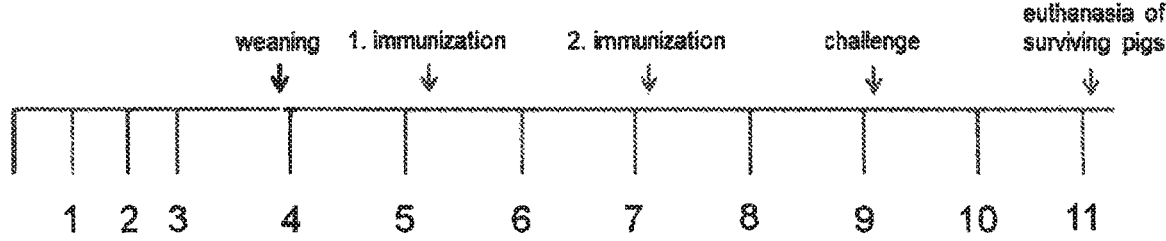

Briefly as shown in FIG. 1, piglets at an age of five weeks were prime vaccinated with a rIdeSsuis vaccine. At an age of 7 weeks these piglets were boostered with rIdeSsuis and in one group also prime vaccinated with a bacterin by intramuscular injection (given in the table in FIG. 1). One group of piglets was only prime vaccinated with a bacterin at an age of 7 weeks and a last group of animals was vaccinated twice with a placebo consisting of buffer and adjuvant. The piglets were challenged two weeks after the second immunizations intranasally. Animals were further monitored every eight hours. For reasons of animal welfare, animals were euthanized in any case in which a piglet exhibits high fever in combination with apathy and anorexia as well as in the case of clinical signs of acute polyarthritis or severe meningitis.

All surviving piglets were sacrificed at 14 days post infection.

Figure 2:
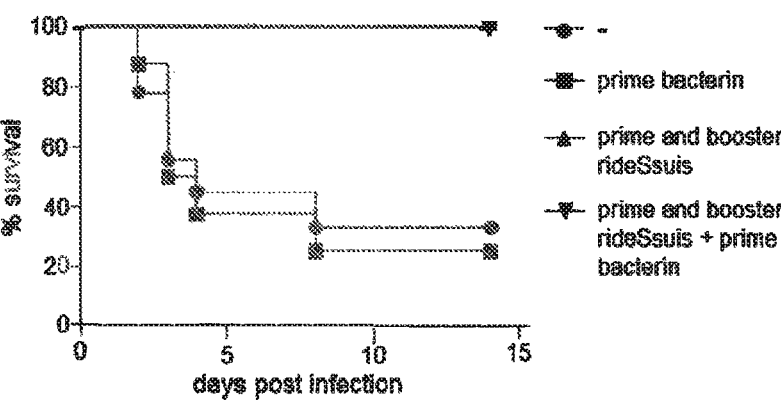

The experiment revealed that the immunization of piglets by using the recombinant protein rIdeSsuis by itself is enough to protect piglets from infections by *S. suis* serotype 2 (FIG. 2).

Example 2

In this example, the bactericidal assay has been used to evaluate the effectiveness of a given vaccine. This test involves the determination of the survival of *S. suis* bacteria of a certain serotype after adding the same to the blood of a test animal. If antibodies protective against a certain sero-type are present in the blood of this test animal, the bacteria will be killed during an incubation time of 2 hours efficiently. The extent of protection is designated as "survival factor" (SF) and is the ratio of the colony count after 120 min, and the colony count directly after adding the bacteria to the blood of the test animal. A low survival factor means an efficient killing of the bacteria in the blood and, therefore, an effective protection of the test animal.

The expression and purification of recombinant IdeSsuis (SEQ ID NO: 2), recombinant IdeSsuisB2 (SEQ ID NO: 7) and recombinant IdeSsuis_homologue (SEQ ID NO: 6) was performed by growth of the appropriate strains in LB broth plus ampicillin. Protein expression was induced by adding IPTG. The purification of the recombinant proteins by $Ni^{2+}$-nitrilotriacetic acid affinity chromatography under native conditions was carried out as recommended by the manufacturer (Macherey-Nagel).

Immunization of piglets: Piglets were prime and booster vaccinated with 1.5 ml vaccine containing 0.25 mg rIdeSsuis or 0.25 mg rIdeSsuisB2 or 0.5 mg rIdeSsuis_homologue containing 20% [vol/vol] Emulsigen as an adjuvant.

Figure 5:
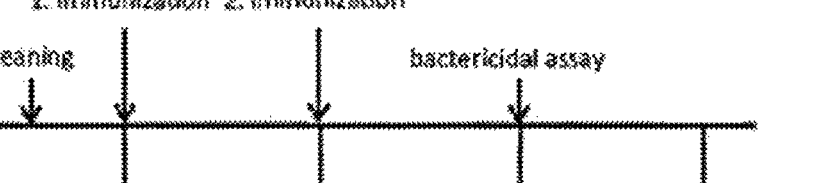
FIG. 5 shows the results of Trial 1.

Trial 1:

Two or four litter mates each are randomly distributed into two trial groups (n=9/group), group 1 control (placebo), group 2 immunized with rIdeSsuis (SEQ ID NO: 2). The animals were immunized and tested according to the test scheme shown in FIG. 5.

Figure 3:
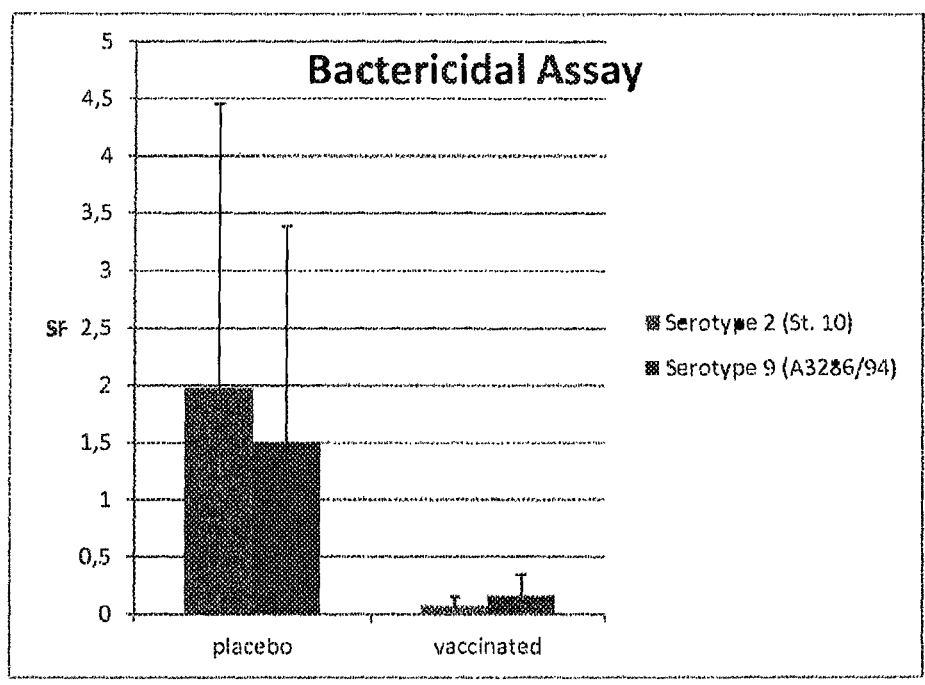

FIG. 3 shows the results which were achieved.

The control group (placebo) showed a much higher survival factor than the vaccinated group. The recombinant antigen rIdeSsuis (group vaccinated), containing the complete sequence of IdeSsuis proteins of serotype 2 strain (SEQ ID NO: 2) induces antibodies effecting an efficient killing of *S. suis* bacteria of strain 2 as well as of strain 9.

Figure 6:
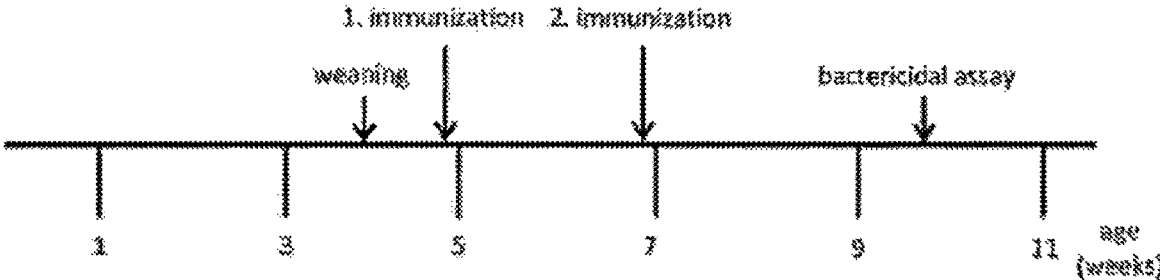
FIG. 6 shows the results of Trial 2.

Trial 2:

Four litter mates each are randomly distributed into four trial groups (n=6/group with the exception of group 4, where n=S), group 1 control (not immunized), group 2 immunized with rIdeSsuis_homologue (SEQ ID NO: 6), group 3 immunized with IdeSsuis derived from serotype 7 strain (rIdeSsuisB2; SEQ ID NO: 7), group 4 immunized with SEQ ID NO: 2. The animals were immunized and tested according to the test scheme shown in FIG. 6.

Figure 4:
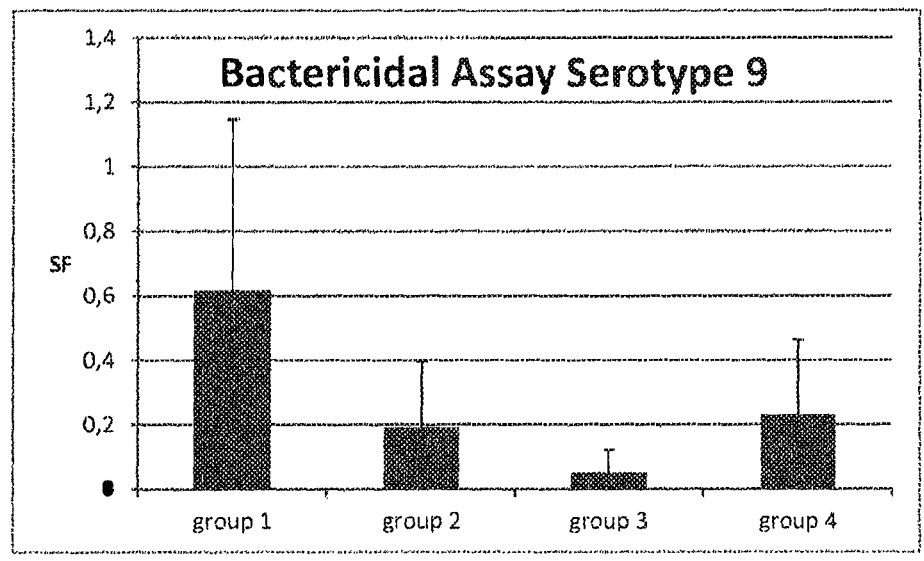

FIG. 4 shows the results which were achieved.

The results show a considerably higher survival factor in the control group (group 1) than in the three vaccination groups. The recombinant antigen rIdeSsuis_homologue (group 2), only containing the N-terminal fragment including the highly conserved Mac-1 domain (IgM-Protease-domain), induced antibodies which result in a much better killing of bacteria compared to the control group. The result of group 2 can be compared with those obtained for group 4. Also antigen rIdeSsuis, containing the complete amino acid sequence of mature IdeSsuis protein of a *S. suis* serotype2 strain induces antibodies which reduce the survival of *S. suis* serotype9 strain in the blood considerably. The survival of serotype9 strain is even more compromised by antibodies which have been induced by antigen rIdeSsuisB2 (group 3).

rIdeSsuisB2 (SEQ ID NO: 7) contains the complete amino acid sequence of the mature IdeSsuis protein of a *S. suis* serotype7 strain and differs in the C terminal half of the protein since it lacks a sequence of 114 aa compared to SEQ ID NO: 1. Aa 80 to 414 of SEQ ID NO: 7 (the highly conserved part of the so-called Mac-1 domain) correspond in 97.9% to the sequence of SEQ ID NO: 5. The identity between remaining (-terminal part of SEQ ID NO: 7 and 1 is 96.4%.

The conclusions which can be drawn from the experimental results are as follows:

rIdeSsuis (SEQ ID NO: 2) provides immune protection across different serotypes of *S. suis,*

An amino acid at least containing the highly conserved Mac-1 domain is sufficient to provide immune protection, Also IdeSsuis proteins of other serotypes, at least containing the highly conserved Mac-1 domain induce protection, even if their overall sequence outside this domain differs from that of the serotype 2 strains (even if certain sequence segments are entirely absent).

40

What is claimed is:

1. A method of inducing neutralizing antibodies in a pig against *Streptococcus suis*, the method comprising administering a vaccine composition comprising (1) a polypeptide consisting of an amino acid sequence selected from SEQ ID NO: 2, SEQ ID NO: 6 and SEQ ID NO: 7; and (2) at least one carrier, and/or at least one diluent, and/or at least one adjuvant.

2. The method of claim 1, wherein the administered vaccine composition comprises from about 0.05 mg to about 2 mg of the polypeptide.

3. The method of claim 1, wherein the administered vaccine composition is formulated for administration to a pig via a route selected from intramuscular, intravenous, subcutaneous, dermal injection, and mucosal application.

* * * * *

SEQUENCE LISTING

```
Sequence total quantity: 14
SEQ ID NO: 1              moltype = AA   length = 1141
FEATURE                  Location/Qualifiers
source                   1..1141
                         mol_type = protein
                         organism = Streptococcus suis
SEQUENCE: 1
MNIQERFSLR KSAVGLVSVS LLCAIYTSTV AADTVVTGVN EIIEESQVKD EVSIESEKNE   60
SLDGSNIEIV EEIADNIPSP VIAEGEVAVE MKVDRGTENV VSRNDTEVTT SEQNQIEVTE  120
TKEILNQTSY QTESGEQRQI IWAHGITPPA MEQSGGFVKE KYGDYLNYTA PFEAGKGYYD  180
TNKSLNASFI DLNLCFAAVS SNMVHWWLEQ NSSYVERYLK EKKGTVNVEE NYAITDLRRY  240
INSFQNQQNS RVFDMFKTYY GYRTNGFVSD ALVDLFINGY KPKAQGGVNL EDSQLVPDSR  300
GGFFYDVFKE KKLTNRIFSG SYERFGEDVR TVLESKGLLG LTYRTLGYAT HIVTVWGAEY  360
DNQGKIKAVY ITDSDDQQEQ IGLKRMGITR DASGNPRLNN HMKNNSAGAL LDYVHTIRLG  420
QDLWEEYFNP LAKAKETASQ TLADTKKALD LSIQGQSELP ESMRLIYLEK LNNLYNQGIL  480
SIQKAESSEM LSGALENGLN SLKSLDFPIS EVGNALAPDL PVGDRSTVSD VDSLSSQETS  540
STNLEADTEN AGIIADGTNQ LHFPVEAQTT SSVEAEGDNV FEQEADTLPI IIENKDEFGS  600
ELSRNMQTSE TDSLVVAVEE DVKNDEVAQV EELLESEKVE NQSSELLSDT LIVESANDKE  660
EDRVEAVVSE QPDSIPHQNV EISLVEPTNV ETETVVTPIN DAATPHGSPT YIDNSVTESV  720
ATPLEKDSIQ AGETEIAEPT SSESTNVETE TVVTPVNDVA TPHGSPTYID NSVTESVATP  780
LEKDSIQAGE TEIAEPTSSE STNVETETVV TPVNDVATPH GSPTYIDNSV TESVATPLEK  840
DSIQAGETEI AEPTSSESTS VEAELVDNSE IHAATSSVTP CGSSAYADGS TTESVATPLE  900
KDSIQTGNTE IAEPTSSKST NVEAASVDNS EIHADASLTA VSSVNLDNPV IEPVAISLIG  960
SKRDTNAEVE VSSLSKREVR KTNTDGLISV QSKVIKKELL ESSLAEAGSP LLEATIAQSS 1020
NSNSTEIGMS YQNTVLLESN NTERQVSKAE IVMEHKETEL VETVSSASEP VVLVENISQT 1080
SNNTIESGKN MGVQSQAGAK QILGVEQSSK VSTPTSRQIM GVGLLTLVLG SALGLLKKRR 1140
K                                                                1141

SEQ ID NO: 2              moltype = AA   length = 1130
FEATURE                  Location/Qualifiers
REGION                   1..1130
                         note = Artificial rIdeSsuis protein sequence
source                   1..1130
                         mol_type = protein
                         organism = synthetic construct
SEQUENCE: 2
MAHHHHHHVG TGSNDDDDKS PDPVVTGVNE IIEESQVKDE VSIESEKNES LDGSNIEIVE   60
EIADNIPSPV IAEGEVAVEM KVDRGTENVV SRNDTEVTTS EQNQIEVTET KEILNQTSYQ  120
TESGEQRQII WAHGITPPAM EQSGGFVKEK YGDYLNYTAP FEAGKGYYDT NKSLNASFID  180
LNLCFAAVSS NMVHWWLEQN SSYVERYLKE KKGTVNVEEN YAITDLRRYI NSFQNQQNSR  240
VFDMFKTYYG YRTNGFVSDA LVDLFINGYK PKAQGGVNLD SQLVPDSRG GFFYDVFKEK  300
KLTNRIFSGS YERFGEDVRT VLESKGLLGL TYRTLGYATH IVTVWGAEYD NQGKIKAVYI  360
TDSDDQQEQI GLKRMGITRD ASGNPRLNNH MKNNSAGALL DYVHTIRLGQ DLWEEYFNPL  420
AKAKETASQT LADTKKALDL SIQGQSELPE SMRLIYLEKL NNLYNQGILS IQKAESSEML  480
SGALENGLNS LKSLDFPISE VGNALAPDLP VGDRSTVSDV DSLSSQETSS TNLEADTENA  540
GIIADGTNQL HFPVEAQTTS SVEAEGDNVF EQEADTLPII IENKDEFGSE LSRNMQTSET  600
DSLVVAVEED VKNDEVAQVE ELLESEKVEN QSSELLSDTL IVESANDKEE DRVEAVVSEQ  660
PDSIPHQNVE ISLVEPTNVE TETVVTPIND AATPHGSPTY IDNSVTESVA TPLEKDSIQA  720
GETEIAEPTS SESTNVETET VVTPVNDVAT PHGSPTYIDN SVTESVATPL EKDSIQAGET  780
EIAEPTSSES TNVETETVVT PVNDVATPHG SPTYIDNSVT ESVATPLEKD SIQAGETEIA  840
EPTSSESTSV EAELVDNSEI HAATSSVTPC GSSAYADGST TESVATPLEK DSIQTGNTEI  900
```

```
AEPTSSKSTN VEAASVDNSE IHADASLTAV SSVNLDNPVI EPVAISLIGS KRDTNAEVEV    960
SSLSKREVRK TNTDGLISVQ SKVIKKELLE SSLAEAGSPL LEATIAQSSN SNSTEIGMSY   1020
QNTVLLESNN TERQVSKAEI VMEHKETELV ETVSSASEPV VLVENISQTS NNTIESGKNM   1080
GVQSQAGAKQ ILGVEQSSKV STPTSRQIMG VGLLTLVLGS ALGLLKKRRK              1130

SEQ ID NO: 3           moltype = DNA  length = 3426
FEATURE                Location/Qualifiers
source                 1..3426
                       mol_type = other DNA
                       organism = Streptococcus suis
SEQUENCE: 3
atgaacattc aagaacgatt ttctttgaga aaatccgcgg ttggcttggt ctcagtctct    60
ttgctatgtg ctatttatac atccactgtt gctgccgata cagttgttac aggagtgaat   120
gaaataattg aagaatcaca agtcaaggat gaggtatcta ttgaatcaga aaaaaatgaa   180
tccctagatg gttctaatat tgaaattgta gaggaaatag cagacaacat cccatcacct   240
gttatcgctg aaggggaagt agcggtagag atgaaagttg acagagggac cgagaatgta   300
gtttctagaa atgatacaga agttacgacg agcgagcaaa atcagataga ggttactgag   360
acaaaagaaa ttttgaatca gaccagttat caaacggaga gtggcgagca acgacaaatt   420
atatgggccc atggaattac tcctcctgca atggaacaaa gcggtggttt tgtaaaggaa   480
aagtatggag actatttaaa ctatacagcg ccatttgagg ctggaaaagg ctactatgat   540
accaataaga gtctgaatgc ttcatttatt gaccttaatc tttgttttgc agctgtgtct   600
tcaaacatgg tacattggtg gttggaacag aatagttcct atgttgagcg atatctcaaa   660
gaaaaaaagg gtacagtaaa tgttgaagaa aactacgcaa taacggactt acggcgctat   720
attaattcat tccaaaatca acaaaatagt cgagttttg atatgttcaa aacttactat   780
ggttatcgta caaatggttt tgtatcagat gccttggttg acttgtttat taacggatat   840
aaacctaagg cacagggcgg tgtcaatctg gaagatagcc agttagtacc agatagtagg   900
ggtggctttt tctacgacgt tttcaaagag aaaaaactga caaatcgaat ttttagtggt   960
agttatgagc ggtttggtga ggatgttcga actgtttttgg aaagcaaagg attactcggc  1020
ttaacttata gaacattagg ttatgcaacg catattgtga cggtatgggg tgctgagtac  1080
gacaatcaag gtaagattaa ggctgtctat atcacagatt ctgatgatca acaagaacaa  1140
attggtttga agcgtatggg aatcactcgt gatgcttccg gaaatccacg tttgaataat  1200
catatgaaaa ataattcagc tggagcgctt ttggattatg tccatacaat ccgtctgggt  1260
caagacttat gggaagaata tttcaatccg cttgcaaaag ccaaagaaac agctagtcag  1320
acattagccg atacaaagaa ggcgttggat ttgtctattc aaggacaatc tgaattgcca  1380
gaatcaatgc gactgattta tcttgaaaaa ctaaataatc tctataatca aggaattcta  1440
tctattcaaa aggcagaaag ttctgagatg ctaagtggtg cattggaaaa tggtttaaat  1500
agtttaaaga gtttagattt tcctatttca gaagttggaa atgctttggc accagattta  1560
ccagtaggtg atcgctcaac ggtttcagat gttgattctc tatcatctca agaaacaagt  1620
tccacaaatt tggaagcaga cacagaaat gcaggtatta ttgcagatgg taccaatcaa  1680
ttgcatttc cagtggaggc ccaaacgaca tcttcagtag aggctgaggg agataatgtt  1740
tttgaacaag aggcagatac attaccaata attattgaaa acaaggatga atttggttca  1800
gaactatcaa gaaacatgca aacgtcagaa acggattcgc tagtagtagc tgttgaagaa  1860
gatgtgaaaa atgatgaggt agcccaagtt gaagagctct ttgaatcaga aaaagttgaa  1920
aatcagagtt cggaacttct gtcagacacc ctaatcgtag agagtgcaaa tgacaaagaa  1980
gaagatagag tggaggcggt tgtttctgaa caaccagact caataccaca tcaaaatgta  2040
gaaatctctc ttgtagaacc aacgaatgtc gaaactgaaa ctgtggtcac tcctattaat  2100
gatgcagcta ctcctcatgg ttccccgacg tatatagata attccgtaac tgaatctgta  2160
gctactccac ttgaaaaaga ctccattcaa gccggggaga cagagattgc agaaccaacc  2220
tcgagcgaat caacgaatgt cgaaactgaa actgtggtca ctcctgttaa tgatgtagct  2280
actcctcatg gttccccgac gtatatagat aattccgtaa ctgaatctgt agctactcca  2340
cttgaaaaag actccattca agccggagag acagaaattg caagaaccaac ctcgagcgaa  2400
tcaacgaatg tcgaaactga aactgtggtc actcctgtta atgatgtagc tactcctcat  2460
ggttccccga cgtatataga taattccgta actgaatctg tagctactcc acttgaaaaa  2520
gactccattc aagccgggga gacagagatt gcagaaccaa cctcgagcga atcaactagt  2580
gttgaagctg aacttgtcga caattctgaa attcatgcag ctacctcttc agttactccc  2640
tgtggctcct cggcatatgc agatggttcc acaactgaat ctgtagccac tccgcttgaa  2700
aaagactcca ttcagactgg aaatacagaa attgcagaac caacctcgag caaatcaact  2760
aatgtagaag ctgcatctgt cgacaattct gaaattcatg cagatgcctc tctaactgct  2820
gtttcatcag ttaatctgga taatccagtg attgaaccag tagctatctc ccttatcggt  2880
tctaagaggg acacgaatgc agaagtagaa gtttcttcat tatcgaaaag agaggttaga  2940
aaaacaaata ctgacgggct aatctctgtt caatcaaaag ttattaagaa agaattgcta  3000
gaatcaagct tagcagaagc agggtctcca ttgctagaag ccaccattgc tcagtcttca  3060
aactcaaata gtactgagat aggtatgagc tatcagaata ctgtgttatt agagtctaat  3120
aatacagcgc gtcaggtgtc taaagcagaa attgttatgg aacacaagga gacagagtta  3180
gttgaaacgg tttcatctgc ttctgagcct gtagtgctcg tagaaaatat ctcacaaacc  3240
tcaaataata ctattgaatc tggtaagaat atgggagttc aatctcaagc aggtgcaaaa  3300
caaatttag cgctagaaca atcttcgaaa gtaagtacac ctacttcaag acagattatg  3360
ggagtcggtc tattgactct tgttcttggt agtgctttag gtttgttaaa gaaaagacgt  3420
aagtaa                                                            3426

SEQ ID NO: 4           moltype = DNA  length = 3393
FEATURE                Location/Qualifiers
misc_feature           1..3393
                       note = Artificial nucleotide sequence encoding rIdeSsuis
source                 1..3393
                       mol_type = other DNA
                       organism = synthetic construct
SEQUENCE: 4
atggcacatc accaccacca tcacgtgggt accggttcga atgatgacga cgacaagagt    60
```

-continued

```
ccggatccag ttgttacagg agtgaatgaa ataattgaag aatcacaagt caaggatgag  120
gtatctattg aatcagaaaa aaatgaatcc ctagatggtt ctaatattga aattgtagag  180
gaaatagcag acaacatccc atcacctgtt atcgctgaag gggaagtagc ggtagagatg  240
aaagttgaca gagggaccga gaatgtagtt tctagaaatg atacagaagt tacgacgagc  300
gagcaaaatc agatagaggt tactgagaca aaagaaattt tgaatcagac cagttatcaa  360
acggagagtg gcgagcaacg acaaattata tgggcccatg gaattactcc tcctgcaatg  420
gaacaaagcg gtggttttgt aaaggaaaag tatggagact atttaaacta tacagcgcca  480
tttgaggctg gaaaaggcta ctatgatacc aataagagtc tgaatgcttc atttattgac  540
cttaatcttt gttttgcagc tgtgtcttca aacatggtac attggtggtt ggaacagaat  600
agttcctatg ttgagcgata tctcaaagaa aaaaaggta cagtaaatgt tgaagaaaac  660
tacgcaataa cggacttacg gcgctatatt aattcattcc aaaatcaaca aaatagtcga  720
gttttttgata tgttcaaaac ttactatggt tatcgtacaa atggttttgt atcagatgcc  780
ttggttgact tgtttattaa cggatataaa cctaaggcac agggcggtgt caatctggaa  840
gatagccagt tagtaccaga tagtaggggt ggctttttct acgacgtttt caaagagaaa  900
aaactgacaa atcgaatttt tagtggtagt tatgagcggt ttggtgagga tgttcgaact  960
gttttggaaa gcaaaggatt actcggctta acttatagaa cattaggtta tgcaacgcat  1020
attgtgacgg tatggggtgc tgagtacgac aatcaaggta agattaaggc tgtctatatc  1080
acagattctg atgatcaaca agaacaaatt ggtttgaagc gtatgggaat cactcgtgat  1140
gcttccggaa atccacgttt gaataatcat atgaaaaata attcagctgg agcgcttttg  1200
gattatgtcc atacaatccg tctgggtcaa gacttatggg aagaatattt caatccgctt  1260
gcaaaagcca aagaaacagc tagtcagaca ttagccgata caaagaaggc gttggatttg  1320
tctattcaag gacaatctga attgccagaa tcaatgcgac tgatttatct tgaaaaacta  1380
aataatctct ataatcaagg aattctatct attcaaaagg cagaaagttc tgagatgcta  1440
agtggtgcat tggaaaatgg tttaaatagt ttaaagagtt tagattttcc tatttcagaa  1500
gttggaaatg ctttggcacc agatttacca gtaggtgatc gctcaacggt ttcagatgtt  1560
gattctctat catctcaaga aacaagttcc acaaatttgg agcagacac agagaatgca  1620
ggtattattg cagatggtac caatcaattg cattttccag tggaggccca aacgacatct  1680
tcagtagagg ctgagggaga taatgttttt gaacaagagg cagatacatt accaataatt  1740
attgaaaaca aggatgaatt tggttcagaa ctatcaagaa acatgcaaac gtcagaaacg  1800
gattcgctag tagtagctgt tgaagaagat gtgaaaaatg atgaggtagc ccaagttgaa  1860
gagcttcttg aatcagaaaa agttgaaaat cagagttcgg aacttctgtc agacacccta  1920
atcgtagaga gtgcaaatga caaagaagaa gatagagtgg aggcggttgt ttctgaacaa  1980
ccagactcaa taccacatca aaatgtagaa atctctcttg tagaaccaac gaatgtcgaa  2040
actgaaactg tggtcactcc tattaatgat gcagctactc ctcatggttc cccgacgtat  2100
atagataatt ccgtaactga atctgtagct actccacttg aaaaagactc cattcaagcc  2160
ggggagacag agattgcaga accaacctcg agcgaatcaa cgaatgtcga aactgaaact  2220
gtggtcactc ctgttaatga tgtagctact cctcatggtt ccccgacgta tatagataat  2280
tccgtaactg aatctgtagc tactccactt gaaaaagact ccattcaagc cggagagaca  2340
gaaattgcag aaccaacctc gagcgaatca acgaatgtcg aaactgaaac tgtggtcact  2400
cctgttaatg atgtagctac tcctcatggt tccccgacgt atatagataa ttccgtaact  2460
gaatctgtag ctactccact tgaaaaagac tccattcaag ccggggagac agagattgca  2520
gaaccaacct cgagcgaatc aactagtgtt gaagctgaac ttgtcgacaa ttctgaaatt  2580
catgcagcta cctcttcagt tactccctgt ggctcctcga catatggagg tggttccaca  2640
actgaatctg tagccactcc gcttgaaaaa gactccattc agactggaaa tacagaaatt  2700
gcagaaccaa cctcgagcaa atcaactaat gtagaagctg catctgtcga caattctgaa  2760
attcatgcag atgcctctct aactgctgtt tcatcagtta atctggataa tccagtgatt  2820
gaaccagtag ctatctccct tatcggttct aagagggaca gcaatctg agtagaagt  2880
tcttcattat cgaaaagaga ggttagaaaa acaaatactg acgggctaat ctctgttcaa  2940
tcaaaagtta ttaagaaaga attgctagaa tcaagcttag cagaagcagg gtctccattg  3000
ctagaagcca ccattgctca gtcttcaaac tcaaatagta ctgagatagg tatgagctat  3060
cagaatactg tgttattaga gtctaataat acagagcgtc aggtgtctaa agcagaaatt  3120
gttatggaac acaaggagac agagttagtt gaaacggttt catctgcttc tgagcctgta  3180
gtgctcgtag aaaatatctc acaaacctca aataatacta ttgaatctgg taagaatatg  3240
ggagttcaat ctcaagcagg tgcaaaacaa attttaggcg tagaacaatc ttcgaaagta  3300
agtacaccta cttcaagaca gattatggga gtcggtctat tgactcttgt tcttggtagt  3360
gctttaggtt tgttaaagaa aagacgtaag taa                                 3393
```

```
SEQ ID NO: 5                  moltype = AA  length = 335
FEATURE                       Location/Qualifiers
REGION                        1..335
                              note = Artificial partial sequence of Mac-1 domain
source                        1..335
                              mol_type = protein
                              organism = synthetic construct
SEQUENCE: 5
MKVDRGTENV VSRNDTEVTT SEQNQIEVTE TKEILNQTSY QTESGEQRQI IWAHGITPPA  60
MEQSGGFVKE KYGDYLNYTA PFEAGKGYYD TNKSLNASFI DLNLCFAAVS SNMVHWWLEQ  120
NSSYVERYLK EKKGTVNVEE NYAITDLRRY INSFQNQQNS RVFDMFKTYY GYRTNGFVSD  180
ALVDLFINGY KPKAQGGVNL EDSQLVPDSR GGFFYDVFKE KKLTNRIFSG SYERFGEDVR  240
TVLESKGLLG LTYRTLGYAT HIVTVWGAEY DNQGKIKAVY ITDSDDQQEQ IGLKRMGITR  300
DASGNPRLNN HMKNNSAGAL LDYVHTIRLG QDLWE                               335
```

```
SEQ ID NO: 6                  moltype = AA  length = 457
FEATURE                       Location/Qualifiers
REGION                        1..457
                              note = Artificial rIdeSsuis_homologue sequence
source                        1..457
                              mol_type = protein
                              organism = synthetic construct
```

```
SEQUENCE: 6
MAHHHHHHVG TGSNDDDDKS PDPVVTGVNE IIEESQVKDE VSIESEKNES LDGSNIEIVE   60
EIADNIPSPV IAEGEVAVEM KVDRGTENVV SRNDTEVTTS EQNQIEVTET KEILNQTSYQ  120
TESGEQRQII WAHGITPPAM EQSGGFVKEK YGDYLNYTAP FEAGKGYYDT NKSLNASFID  180
LNLCFAAVSS NMVHWWLEQN SSYVERYLKE KKGTVNVEEN YAITDLRRYI NSFQNQQNSR  240
VFDMFKTYYG YRTNGFVSDA LVDLFINGYK PKAQGGVNLE DSQLVPDSRG GFFYDVFKEK  300
KLTNRIFSGS YERFGEDVRT VLESKGLLGL TYRTLGYATH IVTVWGAEYD NQGKIKAVYI  360
TDSDDQQEQI GLKRMGITRD ASGNPRLNNH MKNNSAGALL DYVHTIRLGQ DLWEEYFNPL  420
AKACRSTSLR PHSSLVKKPL LRNLNASTWT RLLAQLN                          457

SEQ ID NO: 7            moltype = AA  length = 1016
FEATURE                 Location/Qualifiers
REGION                  1..1016
                        note = Artificial rIdeSsuisB2 sequence
source                  1..1016
                        mol_type = protein
                        organism = synthetic construct
SEQUENCE: 7
MAHHHHHHVG TGSNDDDDKS PDPVVTGVNE IIEESQVKDE VSIESEKNES LDGSNIEIVE   60
EIADNIPSPV IAEGEVAVEM KVDRGTENVV SRNDTEVTTS EQNQIEVTET KEILNQTSYQ  120
TESGEQRQII WAHGITPPAM EQSGGFVKEK YGDYLNYTAP FKAGKGYYDT NKSLNASFID  180
LNLCFAAVSS NMVHWWLEQN SSYVERYLKE KKGTVNVGEN YAITDLRRYI DSFQDQQNSR  240
VFDMFKTYYG YRTNGFVSDA LVDLFINGYK PKVQGGVNLE DSQLVPDSRG GFFYDVFKEK  300
KLTNRIFSGS YERFGEDVRT VLESKGLLGL TYRTLGYATH IVTVWGAEYD NQGKIRAVYI  360
TDSDDQQEQI GLKRMGITRD ASGNPRLNNH VKNNSAGALL DYVHTIRLGQ DLWEEYFNPF  420
AKAKEIASQI LADRKKALVL SIQGQSELPE SMRLIYLEKL NNLYNQGILS IQKTESSEML  480
SGALENGLNS LKSLDFPISE VGNALAPDLS VGDRSTVSDV DSLSSQETSS TNLEADTENA  540
GIIADGTNQL HFPVEAQTTS SVEAEGDNVF EQEADTLPII IENKDEFGSE LSGNMQTSET  600
DSLVVAVEED VKNDEVDQVE KLLESEKVEN QSSELLSDTL IVEGANDKEE DRVEAVVSEQ  660
PDSIPHQNVE ISPVEPMNVE TESVVTPIND AATPHGFPMY IDNSVTESVA TPLEKDSIQA  720
GETEIAEPTS SESTSVEAEL VDNSEIHSAT SSVTPRGSSA YADSSTTESV ATLLEKDSIQ  780
AGETEIAEPT SSKSTNVEAA SVDNSEIHAD TSLTAVSSVN LDNPVIEPVA IPLIGSKRDT  840
NAEVEVSSLS KREVRKPNTE GLISVQSKVI KKELLESSLV EAGSPLLEAT IAQSSNSNST  900
EIGMSYQNTV LLESNNTERQ VSKAEIVIEH KETELVETVS SASEPVVLVE NISQTSNNTI  960
ESGKNMGVQS QAGAKQILGI EQSSKVSTPT SRQIMGVGLL TLVLGSALGL LKKRRK     1016

SEQ ID NO: 8            moltype = DNA  length = 1374
FEATURE                 Location/Qualifiers
misc_feature            1..1374
                        note = Artificial nucleotide sequence encoding
                         rIdeSsuis_homologue
source                  1..1374
                        mol_type = other DNA
                        organism = synthetic construct
SEQUENCE: 8
atggcacatc accaccacca tcacgtgggt accggttcga atgatgacga cgacaagagt   60
ccggatccag ttgttacagg agtgaatgaa ataattgaag aatcacaagt caaggatgag  120
gtatctattg aatcagaaaa aaatgaatcc ctagatggtt ctaatattga aattgtagag  180
gaaatagcag acaacatccc atcacctgtt atcgctgaag gggaagtagc ggtagagatg  240
aaagttgaca gagggaccga gaatgtagtt tctagaaatg atacagaagt tacgacgagc  300
gagcaaaatc agatagaggt tactgagaca aaagaaattt tgaatcagac cagttatcaa  360
acggagagtg gcgagcaacg acaaattata tgggcccatg gaattactcc tcctgcaatg  420
gaacaaagcg gtggttttgt aaaggaaaag tatggagact atttaaacta tacagcgcca  480
tttgaggctg gaaaaggcta ctatgatacc aataagagtc tgaatgcttc atttattgac  540
cttaatcttt gttttgcagc tgtgtcttca aacatggtac attggtggtt ggaacagaat  600
agttcctatg ttgagcgata tctcaaagaa aaaaagggta cagtaaatgt tgaagaaaac  660
tacgcaataa cggacttacg gcgctatatt aattcattcc aaaatcaaca aaatagtcga  720
gttttgata  tgttcaaaac ttactatggt tatcgtacaa atggttttgt atcagatgcc  780
ttggttgact tgtttattaa cggatataaa cctaaggcac agggcggtgt caatctggaa  840
gatagccagt tagtaccaga tagtaggggg ggctttttct acgacgtttt caaagagaaa  900
aaactgacaa atcgaatttt tagtggtagt tatgagcggt ttggtgagga tgttcgaact  960
gttttggaaa gcaaaggatt actcggctta acttatagaa cattaggtta tgcaacgcat 1020
attgtgacgg tatggggtgc tgagtacgac aatcaaggta agattaaggc tgtctatatc 1080
acagattctg atgatcaaca agaacaaatt ggtttgaagc gtatgggaat cactcgtgat 1140
gcttccggaa atccacgttt gaataatcat atgaaaaata attcagctgg agcgcttttg 1200
gattatgtcc atacaatccg tctgggtcaa gacttatggg aagaatattt caatccgctt 1260
gcaaaagcct gcaggtcgac aagcttgcgg ccgcactcga gtctggtaaa gaaaccgctg 1320
ctgcgaaatt gaacgccag cacatggact cgtctactag cgcagcttaa ttaa         1374

SEQ ID NO: 9            moltype = DNA  length = 3051
FEATURE                 Location/Qualifiers
misc_feature            1..3051
                        note = Artificial nucleotide sequence encoding rIdeSsuisB2
source                  1..3051
                        mol_type = other DNA
                        organism = synthetic construct
SEQUENCE: 9
atggcacatc accaccacca tcacgtgggt accggttcga atgatgacga cgacaagagt   60
ccggatccag ttgttacagg agtgaatgaa ataattgaag aatcacaagt caaggatgag  120
```

-continued

```
gtatctattg aatcagaaaa aaatgaatcc ctagatggtt ctaatattga aattgtagag    180
gaaatagcag acaacatccc atcacctgtt atcgctgaag gggaagtagc ggtagagatg    240
aaagttgaca gagggaccga gaatgtagtt tctagaaatg atacagaagt tacgacgagc    300
gagcaaaatc agatagaggt tactgagaca aaagaaattt tgaatcagac cagttatcaa    360
acggagagtg gcgagcaacg acaaattata tgggcccatg gaattactcc tcctgcaatg    420
gaacaaagcg gtggttttgt aaaggaaaag tatggagact atttaaacta tacagcgcca    480
tttaaggcag gaaaaggcta ttatgatacc aataaaagtc tcaatgcttc atttattgac    540
cttaacctat gttttgcagc cgtgtcttcc aacatggtac attggtggtt ggaacagaat    600
agttcctatg ttgagcgata tctcaaagaa aaaaagggta cagtaaatgt tggggaaaac    660
tatgcaataa cggacctacg tcgctatatt gattcgttcc aggatcagca aaatagtcga    720
gtctttgata tgttcaaaac ttactacggt tatcgtacaa atggtttttgt gtcagatgcc    780
ctagttgact tgtttattaa tggatataaa cctaaggtac agggtggtgt caatctggaa    840
gatagccagt tagtaccaga tagtagggggt ggctttttct acgacgtttt caaagagaaa    900
aaactgacaa atcgtatttt tagtggtagc tatgagcgtt ttggtgagga tgttcgaact    960
gttttggaga gcaaaggatt actcggtcta acttatagaa cattaggcta tgcaacgcat   1020
attgtgacgg tatgggggtgc tgagtacgat aatcaaggta agattagggc tgtctatatc   1080
actgattccg atgatcaaca agaacaaatt ggtttgaagc gtatgggaat cactcgtgat   1140
gcttctggaa atccgcgttt gaataatcat gtgaaaaata attcagctgg ggcgcttttg   1200
gattatgtcc atacaatccg tcttggtcaa gacttatggg aagaatattt caatccgttc   1260
gcaaaagcca aagaaatagc tagtcagata ctagctgata gaaagaaggc gttggttctg   1320
tctattcaag gacaatctga attgccagaa tcaatgcggc tgatttatct tgaaaaacta   1380
aataatctct ataatcaagg gattctatct attcaaaaga cgaaagttc tgagatgcta   1440
agtggtgcat tggaaaatgg tttaaatagt ttaaagagtt tagattttcc tatttcagaa   1500
gttggaaatg ctttggcacc agatttatca gtaggtgatc gctcaacggt ttcagatgtt   1560
gattctctat catctcaaga aacaagttcc acaaatttgg aagcagacac agagaatgca   1620
ggtattattg cagatggtac caatcaattg cattttccag tggaggccca aacgacatct   1680
tcagtagagg ctgagggaga taatgttttt gaacaagagc cagatacatt accaataatt   1740
attgaaaaca aggatgaatt tggttcagaa ctatcaggaa acatgcaaac gtcagaaacg   1800
gattcgctag tagtagctgt tgaagaagat gtgaaaaatg atgaggtaga ccaagttgaa   1860
aagcttcttg aatcagaaaa agttgaaaat cagagttcgg aacttctgtc agacaccccta   1920
atcgtagagg gtgcaaatga caaagaagaa gatagagtgg aggcggttgt ttctgaacaa   1980
ccagactcaa taccacatca aaatgtagaa atctctcctg tagaaccaat gaatgtcgaa   2040
actgaatctg tggtcactcc tattaatgat gcagctactc ctcatggttt cccgatgtat   2100
atagataatt ccgtaactga atctgtagct actccacttg aaaaagactc cattcaagcc   2160
ggagagacag aaattgcaga accaacctcg agcgaatcaa ctagtgttga agctgaactt   2220
gtcgacaatt ctgaaatcca ttcagctacc tcttcagtta ctccccgtgg ttcctcggca   2280
tatgcagata gttccacaac tgaatctgta gctactctgc ttgaaaaaga ctccattcag   2340
gctggagaga cagaaattgc agaaccaacc tcgagcaaat caactaatgt cgaagctgca   2400
tctgtcgaca attctgaaat tcatgcagat acctctctaa ctgctgtttc atcagtcaat   2460
ctggataatc cagtgattga accagtagct atccccctta tcggttctaa gagggacacg   2520
aatgcagaag tggaagtttc ttcattatcg aaaagagagg ttagaaaacc aaatactgaa   2580
gggctaatct ctgttcaatc aaaagttatt aagaaagaat tgctagaatc aagcttagta   2640
gaagcagggt ctccattgct agaagccacc attgctcagt cttcaaactc aaatagtact   2700
gagataggta tgagctatca gaatactgtg ttattagagt ctaataatac agagcgtcag   2760
gtgtctaaag cagaaattgt tatagaacac aaggagacag agttagttga aacgggtttca   2820
tctgcttctg agcctgtagt gctcgtagaa aatatctcac aaacctcaaa taatactatt   2880
gaatctggta gaaatatggg agttcaatct caagcaggtg caaaacaaat tttaggcata   2940
gaacaatctt cgaaagtaag tacacctact tcaagacaga ttatgggagt cggtctattg   3000
actcttgttc ttggtagtgc tttaggtttg ttaaagaaaa gacgtaagta a            3051
```

```
SEQ ID NO: 10           moltype = AA  length = 335
FEATURE                 Location/Qualifiers
REGION                  1..335
                        note = amino acids 91 to 425 of WP_044671938
source                  1..335
                        mol_type = protein
                        organism = synthetic construct
SEQUENCE: 10
MKVDRGTENV VSRNDTEVTT SEQNQIEVTE TKEILNQTSY QTESGEQRQI IWAHGITPPA     60
MEQSGGFVKE KYGDYLNYTA PFKAGKGYYD TNKSLNASFI DLNLCFAAVS SNMVHWWLEQ    120
NSSYVERYLK EKKGTVNVGE NYAITDLRRY IDSFQDQQNS RVFDMFKTYY GYRTNGFVSD    180
ALVDLFINGY KPKVQGGVNL EDSQLVPDSR GGFFYDVFKE KKLTNRIFSG SYERFGEDVR    240
TVLESKGLLG LTYRTLGYAT HIVTVWGAEY DNQGKIKAVY ITDSDDQQEQ IGLKRMGITR    300
DASGNPRLNN HMKNNSAGAL LDYVHTIRLG QDLWE                              335
```

```
SEQ ID NO: 11           moltype = AA  length = 335
FEATURE                 Location/Qualifiers
REGION                  1..335
                        note = amino acids 91 to 425 of WP_002935529
source                  1..335
                        mol_type = protein
                        organism = synthetic construct
SEQUENCE: 11
MKVDRGTENV VSRNDTEVTT SEQNQIEVTE TKEILNQTSY QTESGEQRQI IWAHGITPPA     60
MEQSGGFVKE KYGDYLNYTA PFKAGKGYYD TNKSLNASFI DLNLCFAAVS SNMVHWWLEQ    120
NSSYVERYLK EKKGTVNVGE NYAITDLRRY IDSFQDQQNS RVFDMFKTYY GYRTNGFVSD    180
ALVDLFINGY KPKVQGGVNL EDSQLVPDSR GGFFYDVFKE KKLTNRIFSG SYERFGEDVR    240
TVLESKGLLG LTYRTLGYAT HIVTVWGAEY DNQGKIRAVY ITDSDDQQEQ IGLKRMGITR    300
DASGNPRLNN HVKNNSAGAL LDYVHTIRLG QDLWE                              335
```

-continued

```
SEQ ID NO: 12          moltype = AA  length = 335
FEATURE                Location/Qualifiers
REGION                 1..335
                       note = amino acids 92 to 426 of WP_015647040
source                 1..335
                       mol_type = protein
                       organism = synthetic construct
SEQUENCE: 12
MKVDRGTENV VSRNDKEVTT SEKNQIEVTE TKEILNQTSY QTESGEQRQI IWAHGITPPA  60
MEQSGGFVKE KYGDYLNYTA PFEAGKGYYD TNKSLNASFI DLNLCFAAVS SNMVHWWLEQ  120
NSSYVERYLK EKNSTVNVGE NYAITDLRRY INSFQNQQNS RVFDMFKTYY GYRTNGFVSD  180
ALVDLFINGY KPKAQGGVNL EDSQLVPDSR GGFFYDVFKE KKLTNRIFSG SYERFGEDVR  240
TVLESKGLLG LTYRTLGYAT HIVTVWGAEY DNQGKIAVY ITDSDDQQEQ IGLKRMGITR  300
DASGNPRLNN HVKNNSAGAL LDYVHTIRLG QDLWE                            335

SEQ ID NO: 13          moltype = AA  length = 335
FEATURE                Location/Qualifiers
REGION                 1..335
                       note = amino acids 92 to 426 of WP_023370787
source                 1..335
                       mol_type = protein
                       organism = synthetic construct
SEQUENCE: 13
MKSDNGDENA VSRDDSEVTT NEQNQIEVTE TKEILNQTSY QTESGEQRQI IWAHGITPPA  60
MEQSGGFVKE KYGDYLNYTA PFEAGKGYYD TNKSLNASFI DLNLCFAAVS SNMVHWWLEQ  120
NSSYVERYLK EKKGTVNVEE NYAITDIRRY INSFQNQQNS RVFDMFKTYY GYRTNGFVSD  180
ALVDLFINGY KPKSQGGVNL EDSHLVPDSR GGFFYDVFKE KKLTNRIFSG SYERFGEDVR  240
TVLESKGLLG LTYRTLGYAT HIVTVWGAEY DNQGKIKAVY ITDSDDQQEQ IGLKRMGITR  300
DASGNPRLNN HMKNNSAGAL LDYVHTIRLG QDLWE                            335

SEQ ID NO: 14          moltype = AA  length = 335
FEATURE                Location/Qualifiers
REGION                 1..335
                       note = amino acids 92 to 426 of WP_044678723
source                 1..335
                       mol_type = protein
                       organism = synthetic construct
SEQUENCE: 14
MNSDNGDENV VSRDDSEVTT NEQNQIEVTE TKEILNYTSY QTESGEQRQI VWAYGITPPV  60
MEQKGGFVKE KYGDYLNYTA PFEAGKGYYD TNKSLNASFI DLNLCFAAVS SNMVHWWLEQ  120
NSSYVERYLK EKKGTVNVEE NYAITDLRRY INSFQNQQNS RVFDMFKTYY GYRTNGFVSD  180
ALVDLFINGY KPKAQGGVNL EDSQLVPDSR GGFFYDVFKE KKLTNRIFSG SYERFGEDVR  240
TVLESKGLLG LTYRTLGYAT HIVTVWGAEY DNQGKIKAVY ITDSDDQQEQ IGLKRMGITR  300
DASGNPRLNN HMKNNSAGAL LDYVHTIRLG QDLWE                            335
```